United States Patent [19]

Horikoshi et al.

[11] 3,956,064

[45] May 11, 1976

[54] DEOXYRIBONUCLEASE AND PROCESS FOR ITS PREPARATION

[75] Inventors: Koki Horikoshi; Tadahiko Ando, both of Tokyo; Koichi Yoshida, Hino, all of Japan

[73] Assignee: Rikagaku Kenkyusho, Japan

[22] Filed: Oct. 4, 1974

[21] Appl. No.: 512,058

[30] Foreign Application Priority Data

Oct. 11, 1973 Japan .............................. 48-114131

[52] U.S. Cl. ............................... 195/28 N; 195/62; 195/66 R
[51] Int. Cl.² .................... C12D 13/06; C07G 7/02; C12D 13/10
[58] Field of Search............ 195/62, 65, 66 R, 28 N, 195/29

[56] References Cited

FOREIGN PATENTS OR APPLICATIONS 20,388   4/1969   Japan

Primary Examiner—Lionel M. Shapiro
Attorney, Agent, or Firm—Bucknam and Archer

[57] ABSTRACT

A new deoxyribonuclease (DNase) having preservability and high temperature stability is provided by cultivating a new strain M-26 of the genus Bacillus in an alkaline culture medium. The DNase has such a specificity that it very selectively cleaves phosphodiester bonds between deoxyguanosine and deoxyguanosine in a molecule of deoxyribonucleic acid (DNA) while leaving phosphate groups at the 5'-position.

5 Claims, 4 Drawing Figures

DEOXYRIBONUCLEASE AND PROCESS FOR ITS PREPARATION

FIELD OF THE INVENTION

This invention relates to a deoxyribonuclease which selectively cleaves phosphodiester bonds between specific bases of deoxyribonucleic acid, and to a process for preparing said nuclease by cultivating a deoxyribonuclease-yielding strain of the genus Bacillus in an alkaline medium, and recovering said deoxyribonuclease from the resulting culture broth.

In recent years, great importance has been attached to a study of methods for splitting up nucleic acid by enzymes as well as to the discovery and commercial production of tasteful nucleotides (5'-inosinic acid, 5'-guanylic acid) and a number of research results relating to the structures and functions of deoxyribonucleic acid (DNA) and ribonucleic acid (RNA) which biologically play an important role. As a result, a very large number of nucleases of various kinds have been isolated from various biological materials. The characteristics of these enzymes have been investigated, and some of them have been utilized as agents for decomposing nucleic acid, and also as biochemical reagents.

DESCRIPTION OF THE PRIOR ART

As regards enzymes which decompose RNA, there was established a method for producing 5'-inosinic acid and 5'-guanylic acid by decomposing yeast RNA using an enzyme produced by the genus Streptomyces or filamentous fungi of the genus Penicillium. Furthermore, an enzyme RNase T1 that cleaves a phosphodiester bond adjacent to guanylic acid of RNA selectively was isolated from Takadiastase (a mixed enzyme preparation obtained from a cultivation product of Aspergillus oryzae), and by using it conjointly with RNase of pancreas, the structure of a number of transfer RNA (nucleotide arrangement) were determined.

On the other hand, enzymes obtained from pancreas and hearts or enzymes of snake venom have generally been used as deoxyribonucleases. Very recently, however, enzymes which specifically decompose DNA chains and enzymes which exhibit a different reaction mechanism were discovered. Thus, for example, an enzyme selectively decomposing a single chain DNA, an enzyme decomposing one chain of a double-stranded DNA from its end, an enzyme providing a single-strand breaks in a double-stranded DNA, an enzyme inducing double-stranded scission in double-stranded DNA simultaneously, an enzyme acting only on DNA of special living species, an enzyme showing specificity to DNA that has been irradiated with radioactive rays, and an enzyme showing specificity to the base sequence of DNA have been reported. Of these, the enzyme that shows specificity to the base sequence is an enzyme which selectively or preferentially cleaves phosphodiester bonds between specific bases in a molecule of DNA, and has been considered as essential for investigating the structure of DNA.

Enzymes (deoxyribonuclease (DNase)) which decompose dioxyribonucleic acid (DNA) exist in various living bodies, and a very wide variety of such enzymes have heretofore been isolated from the tissues of animals and plants and cultivated products of microorganisms.

Of these, enzymes that have some extent of specificity to the primary structure of DNA, that is, its nucleotide (base) sequence, and cleave bonds between specific sases relatively preferentially were reported in a Japanese language publication entitled "Biochemistry", Vol. 41, No. 11, pages 749 – 760, 1969. However, this literature reference does not disclose DNase having a definite specificity.

Japanese Patent Publications Nos. 20,388/69 and 6,834/71 disclose that DNase $K_1$ and DNase $K_2$ separated from the cultured cells of Aspergillus oryzae are enzymes which cleave phosphodiester bonds between deoxyguanosine and deoxyguanosine, and between deoxyguanosine and deoxyadenosine, of a molecule of DNA relatively preferentially, and prove effective for a study of the structure and function of DNA. However, these enzymes have the defect that their stability is not satisfactory, and they are relatively difficult to produce on a mass-production basis because they are endoenzymes.

Accordingly, from the viewpoint of commercial production of enzymes and their feasibility as biochemical reagents, the discovery of enzymes having high stability endurable to high temperature treatments and long periods of storage has been desired.

SUMMARY OF THE INVENTION

We have extensively worked for DNase which with the elimination of the defects of the prior art described above, decomposes DNA specifically and has high temperature stability. Consequently, we have found that by cultivating a new strain of the genus Bacillus in an alkaline culture medium, a novel DNase having great temperature stability and good storability for prolonged periods of time can be recovered, which has such a specificity that it very selectively cleaves phosphodiester bonds between deoxyguanosine and deoxyguanosine in a molecule of DNA while leaving phosphate groups at the 5'-position. This discovery led to the present invention.

As will be described in detail hereinbelow with regard to physicochemical properties, this new enzyme has the properly of very preferentially cleaving phosphodiester bonds between deoxyguanosine and deoxyguanosine (G—G) in a molecule of DNA and exhibits high stability, and can be produced in a high yield in a culture liquid of basophilic bacteria. Since this enzyme can act both on a double-stranded DNA and a single-strand DNA and preferentially cleave G—G to form DNA fragments, it can be used for a study of the structure of various high-molecular-weight deoxyribonucleic acids. Furthermore, by using this enzyme, various oligonucleotides having deoxyguanosine at their ends can be prepared. Thus, there can be obtained products which are very useful as medicines or seasonings.

Accordingly, it is an object of this invention to provide highly active DNase which hydrolyzes DNA specifically and has high storage stability.

Another object of this invention is to disclose M-29 Strain which is a deoxyribonuclease-yielding strain belonging to the genus Bacillus.

Still another object of this invention is to provide cultivation conditions for preparing the above DNase by cultivating the above strain.

Still another object of the invention is to provide a process for decomposing nucleic acids using the above enzyme.

A further object of this invention is to provide a method for treating a decomposition liquid resulting from the decomposition of nucleic acids so as to recover the decomposition products.

DESCRIPTION OF PREFERRED EMBODIMENTS

Figure 1:
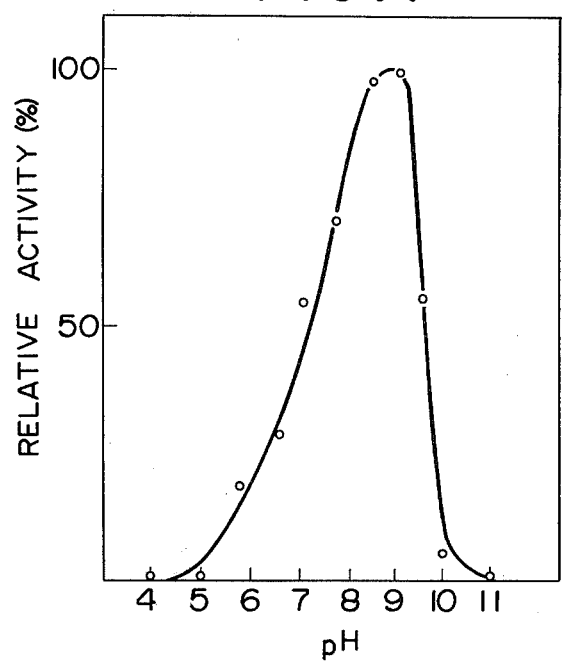
FIG. 1 is a graphic representation showing the optimum pH of the deoxyribonuclease obtained by the process of this invention.

The microorganism used in the process of this invention is a DNase-yielding strain belonging to the genus Bacillus, which is to be cultivated in an alkaline culture medium containing carbonate salts, and the strain No. M-29 of the genus Bacillus to be described can be effectively used in the process of this invention.

Needless to say, any nature or artificial mutants of the strain No. M-29 of the genus Bacillus can be used in this invention so long as they have the ability to produce the DNase of this invention.

The above No. M-29 strain of the genus Bacillus (to be referred to hereinbelow simple as "M-29 strain") was isolated by the inventors of the present application from the soil in Hirosawa, Wako-city, Saitama-Prefecture, Japan. The above No. M-29 strain has been deposited with the American Type Culture collection (ATCC) at 1230/Parklawn Drine, Rockville, Md. 20852 U.S.A. as ATCC access number 31,084, in unrestricted condition permitting the public to have full access to the cultures, as of Sept. 23rd, 1974. All restrictions on the availability of the culture deposit to the public will be irrevocably removed upon the granting of a patent from this application. Further, the above culture will be maintained by the depositor throughout the effective life of the patent.

As will be described later on, the M-29 strain has microbiological properties that can be distinguished from those of any known strains, and is thus found to be a new strain of the genus Bacillus.

This M-29 strain can be conveniently cultivated in an alkaline culture medium having a pH of 7.0 to 11.0, preferably 9.0 to 10.5 in the presence of a carbonate salt to produce DNase.

The tests and classifications in determining the microbacteriological properties of the M-29 strain were based on the methods disclosed in N. R. Smith, R. E. Gordon and F. E. Clark, "Aerobic Spore-Forming Bacteria" (U.S. Department of Agriculture, Nov. 1952) and Bergey's Manual of Determinative Bacteriology, 1957.

Bacteriological Properties a. Morphology:

The size of the vegetative cell is $0.5-0.7\mu \times 2.0-4.0\mu$. This strain is a bacillus and forms spores nearly at the ends of the cells. The spores have a size of $0.8-0.1\mu \times 1.0-1.5\mu$, and oval. the sporangia are definitely swollen. It has pertrichous flagella and exhibits motility.

The Gram's stain is positive. No. acid-fastness.

The above morphological study was made by observing the state of growth of the strain in a culture medium consisting of 10 g of sodium carbonate, 5 g of peptone, 5 g of yeast extract, 20 g of starch, 1 g of $K_2HPO_4$, 0.2 g of $MgSO_4 \cdot 7H_2O$, 15 g of agar and 1 liter of water.

b. State of growth in culture media:

The state of growth in various culture media are shown in Table 1.

Table 1

| Type of culture medium | State of growth | |
|---|---|---|
| | pH of culture medium | |
| | pH 7.0 | pH 10.0* |
| Bouillon liquid culture | Grows slightly | Growth turbid; sediment; no membranous |
| Bouillon-agar plate culture | Poor growth | Circular, flat or raised; and entire edged; the surface is smooth, and semitransparent; opaque |
| Bouillon-agar slant culture | Poor growth | Spreading with the end being dull and the central part lustrous; opaque and semitransparent, and no pigment in the culture medium |
| Bouillon-gelatin stab culture | No liquefaction of gelatin is observed | Liquefied in stratiform |
| Litmus milk | Slightly turns red, but no coagulation of milk is observed | Grows but no coagulation of milk is observed; and since the culture medium is alkaline, no discoloration of litmus is observed. |

*The pH of each of the media was adjusted to 10.0 by adding 1% $Na_2CO_3$.

c. Physiological properties:

Observation was made with regard to culture media obtained by adding 1% $Na_2CO_3$ to the culture media described in the above-cited N. R. Smith et al. reference.

| | | |
|---|---|---|
| 1. Reduction of nitrate: | | yes |
| 2. Denitration reaction: | | no denitration reaction was recognized |
| 3. MR test: | Since the culture medium was alkaline, discoloration of methyl red was not observed. | |
| 4. VP test: | | negative |
| 5. Formation of indole: | | no |
| 6. Formation of hydrogen sulfide: | | no |
| 7. Hydrolysis of starch: | | yes |
| 8. Utilization of citric acid: | | slightly utilized |
| 9. Utilization of nitrate and ammonium salt: | | slightly utilized |
| 10. Formation of pigment: | | no |
| 11. Urease: | | positive |
| 12. Oxidase: | | positive |
| 13. Catalase: | | positive |
| 14. Optimum pH range: | | about 10.0 |
| 15. Optimum temperature range: | | 35 to 50°C. |
| 16. Requirement of oxygen: | | aerobic |
| 17. O-F test: | growth is observed in an aerobic condition to form acid | |
| 18. Utilization of carbon source: | utilizes lactose, arabinose, xylose, glucose, mannose, inositol, fructose, galactose, maltose, sucrose, trehalose, mannitol and starch, to produce acid; no gas is observed; sorbitol and glycerol are not utilized | |
| 19. Resistance to sodium chloride: | | |

-continued slightly grown on 5% sodium chloride

The above bacteriological properties were compared with those of known strains of the genus Bacillus. It has been found that the M-29 strain is similar to *Bacillus circulans* because its sporangia are definitely swollen, its spores are oval, it does not produce gas from a carbon source nor does it produce indole, its Voges-Proskauer reaction (VP test) is negative, and it does not grow at 65°C. However, they apparently differ from each other in their characteristic properties in that while the M-29 strain is Gram-positive, *Bacillus circulans* is Gramnegative, and the growth pH is 7.0–11.0 (optimum pH being about 10.0) for the M-29 strain but about 5.5 for *Bacillus circulans*.

Since the M-29 strain is clearly distinguished from the known strain in view of the above characteristic properties, especially of the fact that the optimum pH for growth of this strain is about 10 which is on the alkaline side, it has been concluded that it would be reasonable to determine it as a new strain belonging to the genus Bacillus.

The culture medium used in this invention may either be solid or liquid, but in either case, it should be an alkaline culture medium containing a carbonate salt, which has a pH of 7.0 to 11.0, preferably 9.0 to 10.5. Thus, there is used a culture medium containing a carbon source, a nitrogen source and inorganic salts, etc. which are required for the growth of microorganisms to which a carbonate salt has been added. For example, a culture medium prepared by adding a carbonate salt to a composition containing soluble starch, peptone, yeast extract, $K_2HPO_4$ and $MgSO_4 \cdot 7H_2O$ is used. Examples of the usable carbonate salt are anhydrous sodium carbonate, potassium carbonate, and sodium bicarbonate. Desirably, the concentration of the carbonate added is 0.5 to 1.5%. The following experimental fact clearly demonstrates that a carbonate salt should be added to the above culture medium to shift its pH to an alkaline side.

A typical formulation of culture medium is illustrated in which only essential C, N, P and N components are shown in percentage in weight to 100 parts of water.

| | |
|---|---|
| Starch | 0.5 – 5% |
| $K_2HPO_4$ | 0.02 – 0.2% |
| Yeast Extract | 0.1 – 1.0% |
| Pepton | 0.1 – 2.0% |
| Remain | same quantity |

The M-29 strain was inoculated into each of the above culture media to which various carbonate salts were added in the concentrations shown in Table 2, and culture media obtained by removing the carbonate salts from the above culture media, adding 1% of NaCl or KCl, and also adding sodium hydroxide to adjust the pH to 10. It was subjected to shaking culture at 35°C. Then, the growth of this microorganism and the product of DNase were examined. The results are shown in Table 2.

The growth of the microorganisms was measured by filling in a cuvette the culture broth obtained after cultivation for 18 hours, and using light of wavelength of 660 m$\mu$. The activity of DNase is one measured by the method to be described using the culture broth obtained after cultivation for 3 days.

Table 2

| Salts added | pH before cultivation | Growth | Activity of DNase (unit/ml.) |
|---|---|---|---|
| Not added | 7.0 | 0.6 | below 100 |
| | 10.0 | 0.8 | '' |
| NaCl | 7.0 | 0.8 | '' |
| | 10.0 | '' | '' |
| KCl | 7.0 | '' | '' |
| | 10.0 | 1.0 | '' |
| NaHCO$_3$ | | | |
| 0.5% | 9.0 | 1.0 | 1650 |
| 1.0% | 9.2 | 1.1 | 1900 |
| 1.5% | 9.3 | 1.1 | 2050 |
| 2.0% | 9.5 | 1.0 | 1970 |
| Na$_2$CO$_3$ | | | |
| 0.5% | 9.6 | 1.1 | 1600 |
| 1.0% | 10.0 | 1.1 | 2160 |
| 1.5% | 10.2 | 1.2 | 2160 |
| 2.0% | 10.5 | 1.0 | 1980 |
| K$_2$CO$_3$ | | | |
| 0.5% | 9.8 | 1.1 | 1400 |
| 1.0% | 10.2 | 1.1 | 2050 |
| 1.5% | 10.3 | 1.0 | 2050 |
| 2.0% | 10.5 | 1.1 | 1960 |

It can be seen from these results that the presence of carbonate salt in the culture medium is essential for the production of the intended DNase.

The M-29 strain can be favorably cultivated by an aerobic shaking culture or an aeration stirring culture, but other methods of cultivation can also be used. For example, the strain can be subjected to shaking culture for 24 to 96 hours at 30° to 37°C., followed by removing the cells from the culture broth and neutralizing the carbonate salt added to the culture medium using acetic acid or a similar acid. Or without neutralization, a 3- to 4-fold amount of an organic solvent such as methanol is added directly to the culture broth from which the cells have been removed, or ammonium sulfate in an amount of about 500 g per liter of the culture broth is used to salt out the culture broth, whereby the DNase is precipitated. The precipitate is then filtered, dehydrated and dried to form a crude enzyme powder of the DNase.

One example of a method of separating DNase from the resulting crude enzyme powder and purifying it is given below. The crude enzyme powder is first dissolved in water, and then dialyzed overnight with flowing water. When the dialyzed solution is passed through a DEAE cellulose column equilibrated with a 0.01 M Tris-HCl buffer having a pH of 8.0, the DNase is adsorbed to the DEAE cellulose. The DNase adsorbing to the column is then eluted by varying the concentration of sodium chloride from 0.01M to 0.5M. The active portions were collected, and concentrated, followed by gel filtration using Sephandex G-75 and Sephadex G-100. The filtrate is lyophilized to form a purified powder of DNase.

The activity of DNase produced by the process of this invention is measured by the following method.

0.02 ml of enzyme solution (an enzyme solution suitably diluted with a buffer so that its absorbance at 260 m$\mu$ is finally within the range of 0.4 to 0.6), 0.1 ml of each buffer and 0.1 ml of a 2 mg/ml DNA solution are reacted for 30 minutes at 40°C. Then, the reaction is stopped by adding a cold PCA solution (7% perchloric acid solution) in an amount of 0.5 ml. The reaction mixture is allowed to stand for 20 minutes in ice. Furthermore, 2.5 ml of cold water is added, and after thorough stirring, the reaction mixture is centrifuged for 10 minutes at 3,000 rmp. The absorbance of the supernatant portion is measured at 260 mμ. An enzymatic activity of one unit is defined as the enzymatic activity capable of increasing the absorbance at 260 mμ by 0.1 under the above conditions.

DNase of this invention is used to hydrolyze DNA, for example, under the following conditions.

A suitable amount of DNase M-29 is mixed with a substrate obtained by dissolving DNA in a 1/10 M borate buffer having a pH of 8.5 in a concentration of 0.2 to 0.3%, and they are allowed to react at 40°C. for a proper period of time. The amount of the enzyme added and the time required for the reaction differ according to the purpose of use. For example, in order to render DNA completely acidsoluble, 100 units of DNase M-29 is mixed with 1 ml of 1/10 M borate buffer of pH 8.5 containing 0.2% DNA, and they are allowed to react at 40°C for more than 30 minutes. As a result, DNA becomes substantially acid-soluble. In order to cleave DNA partially, the amount of the DNase is changed to about 10 units and the reaction time is shortened to below 30 minutes. Furthermore, an oligonucleotide having G at its end can be obtained by using the DNase M-29. For instance, by passing DNA decomposed with the DNase M29 through a DEAE-urea column, tri-, tetra-, and penta-nucleotides, etc. having G at the end can be separated.

The crude DNase can be stored with good stability at 5°C for 12 months to 24 months or even more. The purified enzyme, in the lyophilized state, is stable at 5°C for more than 6 months. At −20°C, it is stable for more than 12 months.

The physico-chemical properties of the DNase (to be referred to as the present enzyme) will be described below.

1. Activity and substrate specificity:

The present enzyme acts on a single-strand or double-stranded DNA to form an oligonucleotide. The structure of the split portion of the resulting oligonucleotide formed with time by the present enzyme was examined, and the results are shown in Table 3.

Table 3

| Time (minutes) used to hydrolyze DNA by DNase M-29 | Degree of hydrolysis of DNA (%) | Type of terminal nucleotides of oligonucleotides produced by DNase M-29 | | |
|---|---|---|---|---|
| | | Treatment (1) | Treatment (2) | Treatment (3) |
| 45 | 27.8 | — | G | G |
| 70 | 42.8 | — | G | G |
| 90 | 72.2 | — | G | G |
| 120 | 98.9 | (G) | G(A)(T) | G |

Note
Treatment (1): Phosphodiesterase of snake venom was caused to act.
Treatment (2): Alkaliphosphatase, and then phosphodiesterase of snake venom, were caused to act (the 5′ end was detected as a nucleoside).
Treatment (3): Alkali phosphatase, and then pancreatic phosphodiesterase, were caused to act (the 3′ end was detected as a nucleoside)
G: deoxyguanosine
A: deoxyadenosine
T: thymidine
—: showing that no nucleoside was detected
( ): showing that the nucleoside was detected in a trace amount These results demonstrate that the 5′ end and 3′ end of the oligonucleotide formed from DNA by the present enzyme are deoxyguanosine, and the resulting oligonucleotide has 3′—OH and 5′—P groups. Accordingly, this enzyme has such a high degree of specificity that in splitting up DNA to an extent of up to 72%, it cleaves only phosphodiester bonds between deoxyguanosines while leaving the 5′—P groups. When DNA is split up to an extent of about 99%, traces of deoxyadenosine and thymidine are found to exist at the 5′ end, but a greater part (more than 90%) of it is deoxyguanosine. This shows that the present enzyme has very superior specificity.

2. Optimum pH:

The optimum pH range of the present enzyme was examined using an acetic acid salt for pH 4 – 5, a phosphoric acid salt for pH 5 – 8, Tris-HCl for pH 8 – 9, and glycine sodium hydroxide for pH 9 – 11. As can be seen from FIG. 1, the optimum pH of the present enzyme is 7 to 10, especially 9.0. Incidentally, in FIG. 1, the activity of the enzyme at pH 9.0 is considered as 100%.

3. Stable pH range:

The present enzyme (0.01 ml) and 0.025 ml of each buffer of an acetic acid salt (for pH 4 – 5), $KH_2PO_4$ – $Na_2B_4O_7$ (for pH 6 – 9.5), and glycine sodium hydroxide (for pH 9 – 11) are heated for 10 minutes at 50°C. Then, the residual activity of the present enzyme is measured.

Figure 2:
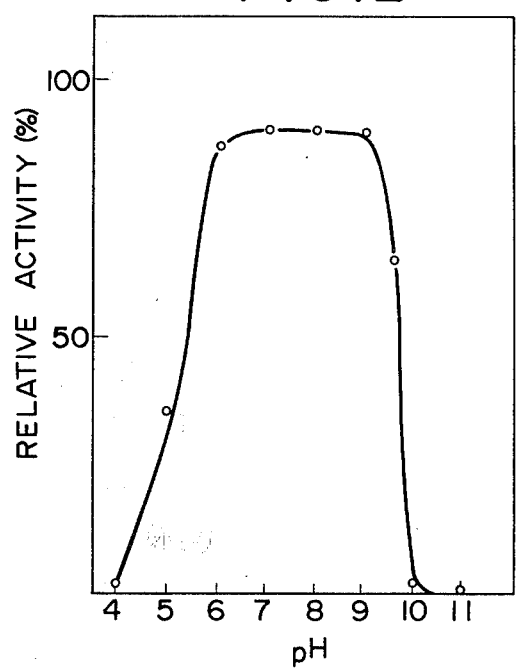
FIG. 2 is a graphic representation showing stable pH of the deoxyribonuclease of this invention.

As is clear from FIG. 2, at a pH of 6 to 9.5, the enzyme is scarcely deactivated even when heated at 50°C for 10 minutes, but remains as a very stable enzyme.

4. Temperature stability:

To 0.01 ml of the present enzyme, 0.025 ml of each buffer of Tris-HCl (pH 9.0) and $KH_2PO_4$—$Na_2B_4O_7$ (pH 9.0) is added, and the mixture is heated at a predetermined temperature for 10 minutes. Then, the residual activity of the present enzyme is measured.

Figure 3:
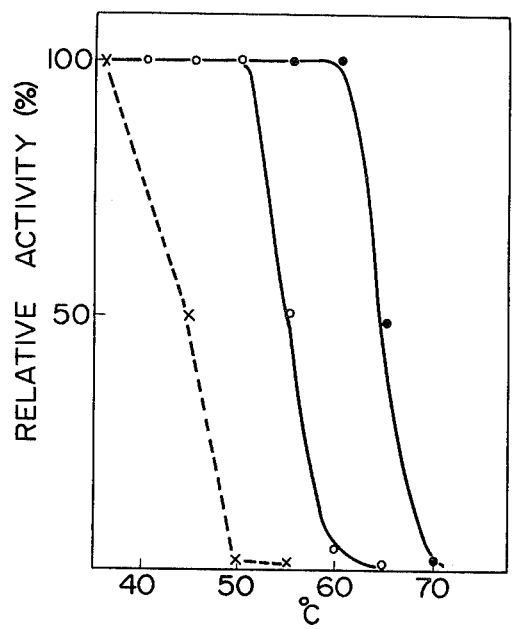
FIG. 3 is a graphic representation showing the temperature stability of the deoxyribonuclease of this invention and the known DNase $K_1$ and DNase $K_2$.

As can be seen from FIG. 3, the present enzyme is very stable to temperature. (In FIG. 3, the symbol O shows the case of using trishydrochloric acid). The result shows that $KH_2PO_4$—$Na_2B_4O_7$, buffer stabilizes the present enzyme (In FIG. 3, the symbol shows the case of using the $KH_2PO_4$—$Na_2B_4O_7$ buffer). On the other hand, the temperature stability of the DNase $K_1$ and DNase $K_2$ was examined in a similar way. The results are shown in a curve marked x in FIG. 3. This supports the stability of the present enzyme.

5. Range of working temperature:

0.2 ml of each of the buffers used in paragraph 4) above and 0.2 ml of the DNA solution are pre-heated for 10 minutes at the pre-determined temperatures. Then, 0.005 ml of the present enzyme suitably diluted is added and reacted for 10 minutes. As is clear from the results shown in FIG. 4, the enzyme acts best at 50° to 60°C.

Figure 4:
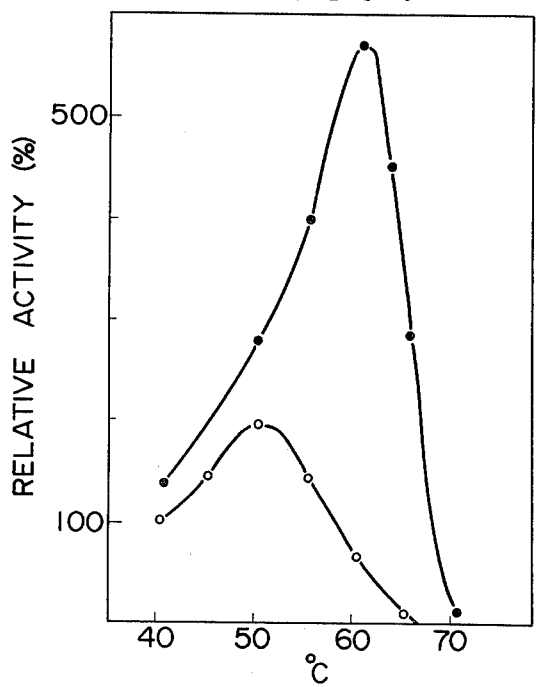
FIG. 4 is a graphic representation showing the range of suitable acting temperature of the deoxyribonuclease of this invention.

Incidentally, in FIG. 4, the enzymatic activity of the enzyme after a 10 minutes' reaction at 40°C using a Tri-HCl buffer is considered at 100%. (In FIG. 4, the symbol "O" shows the case of using Tris-HCl buffer.) It has been confirmed that the $KH_2PO_4$—$Na_2B_4O_7$ buffer activates the present enzyme. (In FIG. 4, the symbol O shows the case of using the $KH_2PO_4$—$Na_2B_4O_7$ buffer.)

6. The method of purification and the method for measuring the activity have already been stated above.

7. Inhibition, activation and stabilization:

There are many examples in which DNase is activated with $Ca^{2+}$, $Mg^{2+}$, or $Mn^{2+}$ (for example, see T. Ando: Biochemica et Bio-physica Acta, 114, 156, 1966). However, the present enzyme is not found to possess these stabilizing and activating activities. As mentioned above, however, the $KH_2PO_4$—$Na_2B_4O_7$ buffer has the action of activating and stabilizing the present enzyme.

The inhibiting action of various metal ions on the present enzyme was examined. Each of the ions indicated in Table 4 was added to the present enzyme so that its final concentration became $2 \times 10^{-3}$ M. The mixture was allowed to stand for 30 minutes at 30°C. Then, the residual activity was measured. The results are shown in Table 4.

Table 4

| Metal ion | Residual activity (%) |
|---|---|
| $Ca^{2+}$ | 106 |
| $Mg^{2+}$ | 100 |
| $Mn^{2+}$ | 88 |
| $Zn^{2+}$ | 71 |
| $Fe^{2+}$ | 81 |
| $Fe^{3+}$ | 47 |
| $Al^{3+}$ | 100 |
| $Co^{2+}$ | 101 |

8. Molecular weight:

The molecular weight of the enzyme was measured by means of gel filtration using Sephadex G-75 and Sephadex G-100. It was found to be about 40,000.

9. Isoelectric point:

The isoelectric point of the enzyme, as determined by electrofocusing method by ampholine and a thin-layer electrophoresis, is not more than pH 4.0.

10. Elemental analysis:

The results of the elemental analysis of the present enzyme are shown in Table 5.

Table 5

| Elements | Weight (%) |
|---|---|
| C | 48.57 |
| H | 7.10 |
| S | 0.63 |
| N | 15.31 |
| Ash | 1.84 |

As described above, the present invention provides a process for preparing a DNA-splitting engyme, characterized by cultivating the specific DNase-yielding strain of the genus Bacillus in an alkaline culture medium containing a carbonate salt, and recovering from the resulting culture broth the resulting novel DNase having temperature stability and such a superior specificity that it cleaves only phosphodiester bonds between specific bases in a molecule of DNA, especially those between deoxyguanosine and deoxyguanosine, while leaving 5'—P groups. According to this invention, this novel DNase can be produced with great advantage.

The following Examples shows the process of this invention as illustrations without limiting the scope of the present invention in any aspect.

EXAMPLE 1

(Composition of culture medium)

| Soluble starch | 20 g |
| $K_2HPO_4$ | 1 g |
| Yeast extract | 5 g |
| Peptone | 5 g |
| $MgSO_4.7H_2O$ | 0.2 g |

The above composition was dissolved in 900 ml of water, and the aqueous solution was sterilized at 115°C for 15 minutes. Separately, 10 g of anhydrous sodium carbonate was dissolved in 100 ml of water, and the aqueous solution was sterilized at 115°C for 15 minutes. The two aqueous solutions sterilized were mixed to form a culture liquor having a pH of 10.5. The culture liquor was poured into a 50 ml shouldered shaking flask (Sakaguchi flask). The M-29 strain (ATCC 31,084) pre-cultivated overnight in the same culture medium was inoculated into the culture liquor in the flask, and cultivated with shaking at 37°C for 72 hours, after which the cells were removed. The amount of DNase obtained was 3,060 units per milliliter of the culture broth.

EXAMPLE 2

520 g of soluble starch, 65 g of polypeptone, 80 g of yeast extract, and 3 g of $K_2HPO_4$ were dissolved in 9 liters of water, and the resulting aqueous solution was placed in a 15-liter jar fermentor. The aqueous solution was sterilized at 115°C for 20 minutes. Then, 1 liter of 10% sodium carbonate separately sterilized was added to form a main culture liquor. One platinum loopful of the M-29 strain (ATCC 31,084) was inoculated into a seed culture liquor (obtained by pouring 200 ml of the culture liquor used in Example 1 into a 2-liter pleated three-necked flask), and cultivated at 37°C for 20 hours with shaking. Then, the culture broth was transferred to the main culture liquor, and cultivation was performed for 54 hours at 35°C at a rotating speed of 800 rpm while passing air at a rate of 10 liters per minute. After the cultivation, the activity of the DNase was measured, and found to be 3,580 u/ml. 9 liters of this culture broth was cooled to 5°C, and then methanol held at −20°C was added so that the concentration of methanol was 50 v/v %. The precipitate obtained was removed by a continuous centrifugal separator. Furthermore, cold methanol was added to the supernatant portion so that the concentration of the methanol became 80 v/v %, and the mixture was allowed to stand at 5°C for 3 hours. The supernatant liquid was gently removed, and then the precipitated portions were collected and thoroughly dehydrated with cold methanol, followed by vacuum drying to afford 146 g of a crude enzyme powder containing 166 u/mg of DNase.

EXAMPLE 3

Example 1 was repeated except that 10 g of glucose was used instead of the soluble starch in preparing the culture medium. The M-29 strain (ATCC 31,084) was cultivated in the same way to afford 1,120 units of DNase per milliliter of the culture broth.

EXAMPLE 4

This Example shows a solid culture of the M-29 strain (ATCC 31,084).

Polypeptone (5 g) and 30 ml of water were added to 30 g of wheat bran, and the mixture was placed in a 500 ml conical flask and sterilized at 115°C for 20 minutes. To the mixture was added 0.3 g of sodium carbonate sterilized by heating, and after thorough mixing, the M-29 strain (ATCC 31,084) was inoculated. The culture broth was allowed to stand at 37°C for 3 days, and then 100 ml of water was added to extract the resulting enzyme. The amount of DNase was 780 units per milliliter of the extract.

1. Process for producing oligonucleotides having terminal group G comprising adding deoxyribonucleic acid in a concentration of 0.2 to 0.3 percentage by weight to a buffer solution having pH 7 – 10 and containing deoxyribonuclease of claim 3 in a concentration of 10 – 100 units, heating the obtained solution for 20 – 50 minutes at a temperature of 35 to 45°C passing the obtained solution through chromatographic column and eluting the oligonucleotides from the column.

2. Process for producing deoxyribonuclease which comprises cultivating a strain of Species M-29 of Genus Bacillus in an alkaline culture medium containing at least one carbonate which is selected from the group of alkali and alkaline earth metal carbonates at pH of 7.0 to 11.0 for about 15 to 120 hours under aerobic conditions, filtering the product to separate the strain, adding methanol or an inorganic salt for salting out the deoxyribonuclease, filtering the obtained precipitate, drying, and purifying.

3. Deoxyribonuclease capable of selectively cleaving the phosphodiester bond between deoxyguanosin and deoxyguanosin in a molecule of deoxyribonucleic acid while the phosphate group remains attached to deoxyguanosin in the 5' position of deoxyribose, said deoxyribonuclease being obtained by cultivating a strain of the new Species M-29 of Genus Bacillus in an alkaline culture medium containing at least one metal carbonate under aerobic conditions followed by separation from the fermentation liquid.

4. The process according to claim 2, wherein the pH in the culture medium is 9–10.5.

5. The process according to claim 2 wherein after filtering to separate the strain, the filtrate is neutralized prior to salting out the deoxyribonuclease.

* * * * *